Nov. 13, 1956 T. E. MOTOSE Plant Pat. 1,527
ROSE PLANT
Filed Dec. 6, 1955
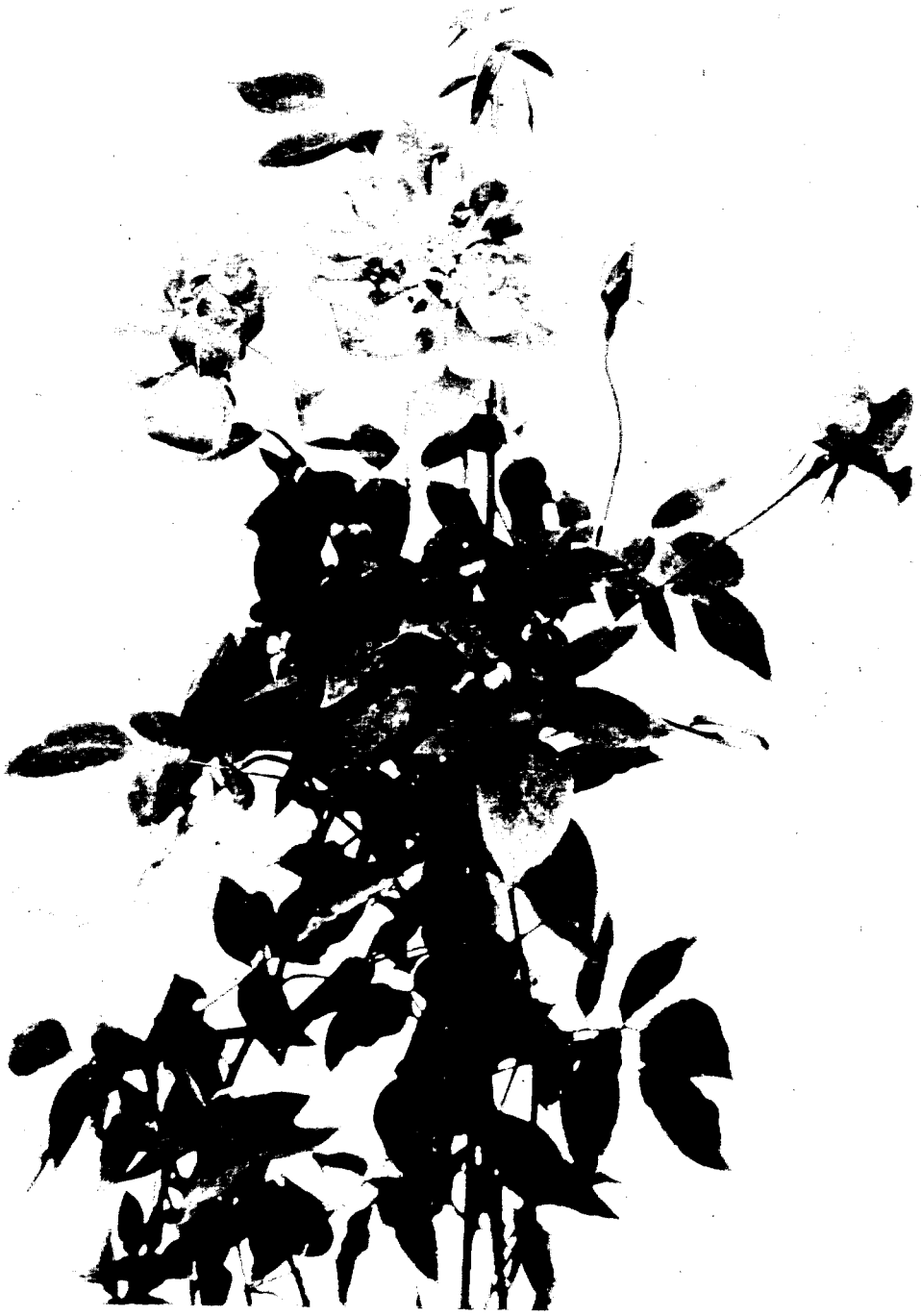
Inventor, Thomas Edison Motose United States Patent Office Plant Pat. 1,527
Patented Nov. 13, 1956

1,527

ROSE PLANT

Thomas Edison Motose, Fairport, N. Y.

Application December 6, 1955, Serial No. 551,462

1 Claim. (Cl. 47—61)

This invention relates to a new and distinct variety of rose plant of the hybrid-tea class, which was originated by me by crossing the known variety Red Columbia (an unpatented hybrid-tea rose) with a seedling (an unpatented rose variety which was a cross of unpatented Red Columbia and an unpatented Tausendschon sport).

My primary object was to produce a recurrent blooming thornless rose plant having Carmine or related colored flowers of different shape. After numerous trials, one of the many seedlings from the cross mentioned in the preceding paragraph was found to be without any thorn, and at the same time bearing the desired colored blooms of unusual shape.

This new variety is distinguished from all other known varieties of roses by the combination of the following characteristics:

(*a*) Thornless canes, branches and stems;

(*b*) Carmine and Tyrian Rose colored blooms;

(*c*) Dark green leaves with very small, simple serrations;

(*d*) Attractively shaped flower (for several days during the early stage of bloom), which may be described as a loose ball of petals resting on five or more large, fully unfurled petals radiating or spreading out in all directions;

(*e*) Abundant production of blooms.

Asexual reproductions of the said new variety by the usual methods of grafting, budding and cutting, performed in Fairport, N. Y., show that the characteristics described in the preceding paragraph, and to be described in the detailed specification that shall follow, come true to form and are fully established and transmitted through succeeding propagations.

The accompanying picture of the new variety shows the typical specimens of flowers, foliage, canes and stems in the various stages of development.

Observations on the new variety for the specific purpose of compiling data for this application were made on sunny days in the month of August, 1955, on plants growing outdoors in my private garden located within the village limit of Fairport, N. Y., except where otherwise indicated.

The color terminology used in describing the new variety is in accordance to Ridgway's Color Standard and Nomenclature (whenever plate number is given) and general meaning of Webster's dictionary (when plate number is not given).

The following is a detailed description of this new variety:

(*a*) *Classification*

*Botanic.*—A hybrid plant belonging to the recurrent or continuous blooming variety, of the cultivated species of the genus Rosa.

*Commercial.*—A bush type hybrid-tea rose plant.

(*b*) *Parentage*

A seedling originated by crossing Red Columbia (seed parent) with another seedling (pollen parent), the latter being a cross of Red Columbia and a large flowered sport of Tausendschon.

All its parents and the parents of its pollen parent are not patented.

(*c*) *Blooming habit*

*Outdoors.*—Recurrent, continuous from early June until stopped by frost in the region of Fairport, N. Y.

*Greenhouse.*—Recurrent, continuous during the healthy life span of the plant.

(*d*) *Flower buds*

*Size.*—Medium (in greenhouse); small (outdoors).

*Shape.*—Ovoid base and with very pointed tip.

*Color of exposed part of petal when sepals begin to divide.*—Carmine (Plate 1) during cool weather, Tyrian Rose (Plate 12) on hot days.

*Color of exposed part of petals when half blown.*—Carmine (Plate 1) during cool weather, Tyrain Rose (Plate 12) on hot days, with slight variations caused by the intensity of sunlight and other known and unknown factors.

*Sepals.*—Very long and frequently with lance-shaped foliaceous appendages; Biscay Green (Plate 17) inside and Spinach Green (Plate 5) outside.

*Calyx.*—Medium in size (in greenhouse), small (outdoors); ovoid and sometimes "pear" shaped; Spinach Green (Plate 5).

*Peduncle.*—Smooth, slender, stiff and Spinach Green (Plate 5).

*Opening characteristics.*—Opens up very well, not affected by normal weather condition found in Fairport, N. Y., during growing seasons.

(*e*) *Flower*

*Size.*—Three and half inches (average) when grown outdoors and fully opened; four and half inches (average) when grown in greenhouse and fully opened.

*Petalage.*—15 to 25 in hot weather; 20 to 30 in cool weather.

*Fragrance.*—Resembles that of a rose named Better Times, Plant Patent Number 23.

*Floral form.*—Intermediate and inner petals forming an attractive, loose, spheroidal shape, and with five or more large, fully unfurled, outer petals radiating or spreading outward from the base of the spheroidal form (during the first few days of bloom); saucer shaped with slight elevation in the central area (during the last stage of bloom).

*Quantity to a stem or flowering branch.*—Usually one.

*Quantity to a bush.*—Many, very high yield of blooms; very little or no difference indoors or outdoors as to quantity (provide there is good sunlight).

*Lasting quality.*—Average hybrid-tea rose bloom.

*Color.*—Carmine (Plate 1) with very narrow white streak running down the middle of some of the inner petals (when heat and sun are not intense); Tyrian Rose (Plate 12) with narrow white streak running down the middle of some of the inner petals (when sunlight is too strong).

*Discoloration.*—Begonia Rose (Plate 1) during the last stage of bloom.

(*f*) *Petals*

*Appearance.*—Satiny inside and shiny outside.

*Shape of outer large petals.*—Egg shaped base, but with the free end very pointed.

*Shape of intermediate petals.*—Egg shaped and with the free end slightly pointed.

*Inner petals.*—Irregular.

*Arrangement.*—Outer petals quite regular, intermediate and inner petals irregular.

*Color.*—Carmine (Plate 1) in cool weather; Tyrian

Rose (Plate 12) when sunlight is too intense; slight variations in the Carmine and Tyrian Rose colors caused by humidity, fertility of soil and other known and unknown factors.

*Lasting quality.*—Average hybrid tea rose petal; drops off cleanly.

(*g*) *Genital organs*

*Stigmas.*—Medium in size; Scarlet (Plate 1), and sometimes light scarlet, on the underside and rim, with a Lemon Chrome (Plate 4) area close around the orifice.

*Styles.*—Thin; uneven in height; Lemon Chrome (Plate 4) toward the base and light scarlet or closely related color toward the upper end.

*Anthers.*—Medium in size, Light Cadmium (Plate 4) in color, and medium in quantity.

*Filaments.*—Medium in length and Carmine (Plate 1) in color, sometimes a light shade of Carmine.

*Pallen.*—Medium in quantity, Light Cadmium (Plate 4) in color.

*Ovaries.*—Enclosed completely as a general rule.

*Hips.*—About 20 millimeter in length (average for indoors and outdoors) and about 10 millimeter in diameter (average for indoors and outdoors) at maturity; Deep Chrome (Plate 3) and often orange-red in color when fully ripe.

*Cell structure.*—Polyploid.

(*h*) *Foliage*

*Form.*—Compound, with three or five leaflets as a general rule.

*Texture.*—Leathery on the underside with ordinary ribs and veins, smooth on the upperside with ordinary ribs and veins.

*Serrations.*—Small, simple and inconspicuous.

*Stipules.*—Narrow and long.

*Rachis.*—Smooth.

*Shape of leaflets.*—Ovoid base and very pointed free end.

*Average size.*—Four and half inches from beginning of stipules to the tip of the terminal leaflet (plants growing outdoors), five and half inches between the same points (plants growing in greenhouse).

*Color.*—Victoria Lake (Plate 1) on the upper surface and Oxblood Red (Plate 1) on the under surface when new or young; Spinach Green (Plate 5) on the upper side and Light Elm Green (Plate 17) on the under side when mature.

(*i*) *Canes and stems*

*Size.*—Medium.

*Characteristics.*—Stiff and strong.

*Bark.*—Smooth.

*Thorns.*—Completely absent.

*Color.*—The lower or older parts of canes—dark green which rarely turns brown; mature or near-mature canes—Spinach Green (Plate 5); very young canes or stems—Scheele's Green (Plate 6) overcast frequently with Oxblood Red (Plate 1).

(*j*) *Plant as a whole*

*Form.*—Bush type.

*Height.*—Two feet, more or less, when grown outdoors in ordinary garden soil in Fairport, N. Y., 4 to six feet when grown in greenhouse.

*Appearance.*—Compact, neat and medium quantity of foliage.

I claim:

A new and distinct variety of rose plant substantially as hereinabove described and disclosed, characterized as to novelty by its thornless canes and branches; by its Carmine and related colored blooms; by the unusual form of its flower which may be described, in its early stage of bloom, as an attractive loose ball of petals resting on five or more large, outer, fully unfurled petals radiating from the base of said ball; by its abundant production of flowers with stiff narrow stem; by its dark, leathery leaves with small, simple serrations.

No references cited.